US009518808B2

(12) United States Patent
Lednev et al.

(10) Patent No.: US 9,518,808 B2
(45) Date of Patent: Dec. 13, 2016

(54) AMMUNITION AND WEAPON TYPE IDENTIFICATION BASED ON SPECTROSCOPIC GUNSHOT RESIDUE ANALYSIS

(75) Inventors: Igor K. Lednev, Glenmont, NY (US); Justin Bueno, New York, NY (US)

(73) Assignee: Research Foundation of State University of New York, Albany, NY (US)

( * ) Notice: Subject to any disclaimer, the term of this patent is extended or adjusted under 35 U.S.C. 154(b) by 803 days.

(21) Appl. No.: 13/578,925

(22) PCT Filed: Feb. 16, 2011

(86) PCT No.: PCT/US2011/025048
§ 371 (c)(1),
(2), (4) Date: Oct. 31, 2012

(87) PCT Pub. No.: WO2011/103161
PCT Pub. Date: Aug. 25, 2011

(65) Prior Publication Data
US 2013/0043130 A1   Feb. 21, 2013

Related U.S. Application Data

(60) Provisional application No. 61/305,010, filed on Feb. 16, 2010.

(51) Int. Cl.
*G01N 21/76* (2006.01)
*F42B 35/00* (2006.01)
*G01N 21/65* (2006.01)

(52) U.S. Cl.
CPC .............. *F42B 35/00* (2013.01); *G01N 21/65* (2013.01)

(58) Field of Classification Search
CPC ........ G01N 21/65; G01N 21/35; G01N 21/55; G01N 21/6458; G01N 33/22; H01J 49/0027; H01J 49/0459; G06K 2009/00946; G06K 9/2018; G06T 5/50; G06T 2207/10152; F42B 35/00; G01J 3/32; G01J 3/44
(Continued)

(56) References Cited

U.S. PATENT DOCUMENTS

| 5,760,898 A | 6/1998 | Haley et al. |
| 7,499,808 B2 | 3/2009 | Sinha |
| 2006/0126168 A1 | 6/2006 | Treado et al. |

OTHER PUBLICATIONS

Croft's MS Thesis: "The Analysis of Unfired Propellant Particles by Gas Chromatography—Mass Spectrometry: a Forensic Approach", School of Physical and Chemical Sciences Queensland University of Technology, Apr. 2008.*
(Continued)

*Primary Examiner* — Yelena G Gakh
(74) *Attorney, Agent, or Firm* — LeClairRyan, a Professional Corporation

(57) ABSTRACT

The present invention relates to a method of identifying ammunition type and/or weapon type used to fire the ammunition from gunshot residue. This method involves providing a sample including a gunshot residue, subjecting the sample to spectroscopic analysis to produce a spectroscopic signature for the sample, and identifying the spectroscopic signature to ascertain the type of ammunition and/or the type of weapon used to fire the ammunition. A method of establishing reference spectroscopic signatures for ammunition type and/or weapon type used to fire the ammunition is also disclosed.

15 Claims, 10 Drawing Sheets

(58) Field of Classification Search
USPC .......................................... 436/164–166, 172
See application file for complete search history.

(56) References Cited

OTHER PUBLICATIONS

Bueno et al., "Raman Spectroscopic Analysis of Gunshot Residue Offering Great Potential for Caliber Differentiation", Anal. Chem., 2012, v. 84, pp. 4334-4339.*
Vandenabeele and Moens, "Micro-Raman spectroscopy of natural and synthetic indigo samples", Analyst, 2003, v. 128, pp. 187-193.*
Brettell et al., "Forensic Science," Analytical Chemistry 81(12):4695-4711 (2009).
Xu et al., "Deaths: Final Data for 2007," National Vital Statistics Reports 58(19):1-136 (2010).
Romolo and Margot, "Identification of Gunshot Residue: A Critical Review," Forensic Science International 119: 195-211 (2001).
Meng and Caddy, "Gunshot Residue Analysis—A Review," J. Forensic Sciences 42(4):553-570 (1997).
Silva et al., "Gunshot Residues: Screening Analysis by Laser-Induced Breakdown Spectroscopy," *J. Brazilian Chem. Soc.* 20(10):1887-1894 (2009).
Garofano et al., "Gunshot Residue—Further Studies on Particles of Environmental and Occupational Origin," Forensic Sci. Int'l. 103(1):1-21 (1999).
Dockey and Goode, "Laser-Induced Breakdown Spectroscopy for the Detection of Gunshot Residues on the Hands of a Shooter," Applied Optics 42(30):6153-6158 (2003).
Santos et al., "Firing Distance Estimation Through the Analysis of the Gunshot Residue Deposit Pattern Around the Bullet Entrance Hole by Inductively Coupled Plasma-Mass Spectrometry—An Experimental Study," Am. J. Forensic Med. Pathol. 28(1 ):24-30 (2007).
Capannesi et al., "Determination of Firing Distance and Firing Angle by Neutron Activation Analysis in a Case Involving Gunshot Wounds," Forensic Sci. Int'l. 61(2-3):75-84 (1993).
Neri et al., "The Determination of Firing Distance Applying a Microscopic Quantitative Method and Confocal Laser Scanning Microscopy for Detection of Gunshot Residue Particles," Int'l. J. Legal Med. 121(4):287-292 (2007).
Brown et al., "Image Analysis of Gunshot Residue on Entry Wounds: II—A Statistical Estimation of Firing Range," Forensic Sci. Int'l. 100(3):179-186 (1999).
Burleson et al., "Forensic Analysis of a Single Particle of Partially Burnt Gunpowder by Solid Phase Micro-Extraction—Gas Chromatography—Nitrogen Phosphorus Detector," J. Chromatography A 1216(22): 4679-4683 (2009).
Nesbitt et al., "Detection of Gunshot Residue by Use of the Scanning Electron Microscope," J. Forensic Sci. 21 :595-610 (1976).
Steffen et al., "Chemometric Classification of Gunshot Residues Based on Energy Dispersive X-ray Microanalysis and Inductively Coupled Plasma Analysis With Mass-Spectrometric Detection," Spectrochimica Acta Part B 62(9):1028-1036 (2007).
Wallace and McQuillan, "Discharge Residues from Cartridge-Operated Industrial Tools," J. Forensic Sci. Soc. 24(5):495-508 (1984).
Ali et al., "In-situ Detection of Single Particles of Explosive on Clothing with Confocal Raman Microscopy," Talanta 78(3):1201-1203 (2009).
Abbott et al., "Resonance Raman and UV-Visible Spectroscopy of Black Dyes on Textiles," Forensic Sci. Int'l. 202(1-3):54-63 (2010).
Hodges and Akhavan, "The Use of Fourier Transform Raman Spectroscopy in the Forensic Identification of Illicit Drugs and Explosives," Spectrochimica Acta Part A 46A(2):303-307 (1990).
Ali et al., "In-situ Detection of Drugs-of-Abuse on Clothing Using Confocal Raman Microscopy," Analytica Chimica Acta 615:63-72 (2008).
Virkler and Lednev, "Raman Spectroscopy Offers Great Potential for the Nondestructive Confirmatory Identification of Body Fluids," Forensic Sci. Int'l. 181:e1-e5 (2008).
Dalby et al., "Analysis of Gunshot Residue and Associated Materials—A Review," J. Forensic Sci. 55(4):924-943 (2010).
Pun and Gallusser, "Macroscopic Observation of the Morphological Characteristics of the Ammunition Gunpowder," Forensic Sci. Int'l. 175:179-185 (2008).
Sharma and Lahiri, "A Preliminary Investigation Into the Use of FTIR Microscopy as a Probe for the Identification of Bullet Entrance Holes and the Distance of Firing," Science & Justice 49:197-204 (2009).
Thissen et al., "Multivariate Calibration with Least-Squares Support Vector Machines," Anal. Chem. 76(11 ):3099-3105 (2004).
Hargreaves et al., "Analysis of Seized Drugs Using Portable Raman Spectroscopy in an Airport Environment—a Proof of Principle Study," J. Raman Spectroscopy 39:873-880 (2008).
Rodger et al., "The In-Situ Analysis of Lipsticks by Surface Enhanced Resonance Raman Scattering," Analyst 123:1823-1826 (1998).
Suzuki et al., "In Situ Identification and Analysis of Automotive Paint Pigments Using Line Segment Excitation Raman Spectroscopy: 1. Inorganic Topcoat Pigments," J. Forensic Sci. 46: 1053-1069 (2001).
Mazzella et al., "Raman Spectroscopy of Blue Gel Pen Inks," Forensic Sci. Int. 152:241-247 (2005).
Grasselli et al., "Chemical Applications of Raman Spectroscopy," New York John Wiley & Sons 2-4 (1981).
Yan et al., "Surface-Enhanced Raman Scattering Detection of Chemical and Biological Agents Using a Portable Raman Integrated Tunable Sensor," Sensors and Actuators B 121:61-66 (2007).
Eckenrode et al., "Portable Raman Spectroscopy Systems for Field Analysis," Forensic Science Communications 3: (2001).
Lednev I. K., "Vibrational Spectroscopy: Biological Applications of Ultraviolet Raman Spectroscopy," in: V. N. Uversky, and E. A. Permyakov, Protein Structures, Methods in Protein Structures and Stability Analysis, Chapter 3.1:1-26 (2007).
Thomas et al., "Raman Spectroscopy and the Forensic Analysis of Black/Grey and Blue Cotton Fibers Part 1: Investigation of the Effects of Varying Laser Wavelength," Forensic Sci. Int. 152:189-197 (2005).
Franke, J. E., "Inverse Least Squares and Classical Least Squares Methods for Quantitative Vibrational Spectroscopy," In Chalmers, eds., Handbook of Vibrational Spectroscopy, vol. 3, New York:John Whiley & Sons, Ltd., pp. 2276-2292 (2001).
Schwoeble and Exline, "Current Methods in Forensic Gunshot Residue Analysis," CRC Press: New York 12-14, 19-20, 32-33, 42-43 (2000).
Sarkis et al., "Measurements of Gunshot Residues by Sector Field Inductively Coupled Plasma Mass Spectrometry—Further Studies With Pistols," Forensic Science International 172: 63-66 (2007).
Malinowski, E. R., Factor Analysis in Chemistry, 3 Ed., New York: John Wiley & Sons, Inc. 17-18 (2002).
Skoog et al., Principles of Instrumental Analysis, 5th Edition. Saunders College Publishing 223-225 (1998).
Stich et al., "Raman Microscopic Identification of Gunshot Residues," J. Raman Spectroscopy 29:787-790 (1998).
Abraham et al., "Application of X-Ray Diffraction Techniques in Forensic Science," Forensic Science Communications 9(2) (2007).
Shashilov et al., "Advanced Statistical and Numerical Methods for Spectroscopic Characterization of Protein Structural Evolution," Chem Rev. 110:5692-5713 (2010).
Wise et al., "PLS Toolbox 3.5 for Use with Matlab.," vol. 17, Eigenvector Research Inc:Manson, Wash.1-254 (2005).
Chemometrics in Spectroscopy, Mark et al., Elsevier, 2-3 (2007).
Chemometrics: From Basics to Wavelet Transformation, Chau et al., Hoboken, N.J.:John Wiley & Sons, Inc, 81-84 (2004).
International Search Report and Written Opinion for PCT/US2011/025048, Sep. 26, 2011, 11 pages.
Zeichner et al., "Application of lead isotope analysis in shooting incident investigations," Forensic Science International 158, 2005, pp. 52-64, Elsevier Ireland Ltd.

(56) References Cited

OTHER PUBLICATIONS

Ng et al., "Detection of Illicit Substances in Fingerprints by Infrared Spectral Imaging," Anal. Bioanal. Chem. 394:2039-2048 (2009).
Ricci et al., "Enhancing Forensic Science with Spectroscopic Imaging," Proc. of SPIE, vol. 6402, 10 pp. (2006).
Jarvis et al., "Genetic Algorithm Optimization for Pre-processing and Variable Selection of Spectroscopic Data," Bioinformatics 21(7):860-868 (2005).
PCT International Search Report and Written Opinion corresponding to PCT/US2014/057802 (mailed Dec. 29, 2014).
Guillory et al., "Confocal Raman Microscopy Analysis of Multilayer Polymer Films," Thermo Scientific (2008) <URL: http://www.revbase.com/tt/sl.achx?z+73090c66&dataid=250130&ft=1>.
Byrne, R., "Course Review—Manufacturing & Testing of PSA Tapes," (2012) <URL: www.gatewayanalytical.com/blog/course-review-manufacturing-testing-of-psa-tapes/>.
Leggett et al., "Gunshot Residue Analysis via Organic Stabilizers and Nitrocellulose," Microchemicals Journal 39:76-85 (1989).
International Preliminary Report on Patentability for corresponding International Application No. PCT/US2014/057802 (Apr. 14, 2016).

\* cited by examiner

AMMUNITION AND WEAPON TYPE IDENTIFICATION BASED ON SPECTROSCOPIC GUNSHOT RESIDUE ANALYSIS

This application is a national stage application under 35 U.S.C. §371 of PCT Application No. PCT/US2011/025048, filed Feb. 16, 2011, which claims the priority benefit of U.S. Provisional Patent Application Ser. No. 61/305,010, filed Feb. 16, 2010, which is hereby incorporated by reference in its entirety.

FIELD OF THE INVENTION

The present invention relates to ammunition and weapon type identification based on gunshot residue (GSR) analysis.

BACKGROUND OF THE INVENTION

An increasing number of analytical techniques have been applied to the field of forensic trace evidence analysis in recent years (Brettell et al., "Forensic Science," *Analytical Chemistry* 81(12):4695-4711 (2009)). New techniques and instrumentation are adapted to the discipline in order to increase the accuracy and efficiency of investigations. The science of "forensic ballistics" is designed to match a suspect to a shooting crime, and is vital to ensuring public safety. According to the Center for Disease Control, firearm related shootings were responsible for over 68% of homicides and were one of the three leading causes of injury related deaths in the United States in 2007 (Jiaquan et al., "Deaths: Final Data for 2007," *National Vital Statistics Reports* 58(19) (2007)). The success of ballistic investigations must act as a deterrent to reduce the number of firearm related crimes in the United States. Matching a suspect to a crime often requires the recovery of some sort of physical evidence, whether it is the projectile (bullet), cartridge case or the actual firearm. Gunshot residue (GSR), or firearm discharge residue (FDR), recovered from several locations around the crime scene, is often utilized not only as physical but chemical evidence.

When a firearm is discharged, a mixture of chemicals is expelled from the barrel and deposited upon both the shooter's hand and around the impact site. This mixture of chemicals includes primers, accelerants, trace metals, and other particles which constitute the gunshot residue (GSR). GSR is not only created as a cloud in the direct vicinity of the gun, but GSR is also propelled in the wake of the bullet in the direction of the target. GSR is obtained from every shooting incident and needs to be analyzed. GSR plays an important role in forensic science in helping to determine certain factors of a shooting and related criminal case.

Gunshot residue (GSR) is caused by the combustion involved in the firing of ammunition. When a gun is fired, the trigger of the gun is pulled causing a firing pin to strike the ammunition (i.e., bullet), crushing the primer. The energy transfer causes explosion of the gun powder sending the bullet through the barrel. The velocity of the bullet is stabilized by a spiraling motion caused by lands and grooves in the barrel called riflings. In a crime laboratory, the riflings are often used to match a bullet to a particular gun provided the bullet-shell is found at the crime scene.

Matching a bullet to the weapon that fired it is a common forensic procedure. The bullet can be matched based upon its impressions caused by the riffling of the barrel, which differs from weapon to weapon. Chemical components of ammunitions also vary between type and size of calibers. Details of the bullet case, propellant, and primer depend upon the manufacturer and the source of ammunition (Romolo and Margot, "Identification of Gunshot Residue: A Critical Review," *Forensic Science International* 119:195-211 (2001)). Generally, for hand guns the larger the caliber the more GSR will be expelled and deposited on the firer's hand (Meng and Caddy, "Gunshot Residue Analysis—A Review," *J. Forensic Sciences* 42(4):553-570 (1997)). An on-site (crime scene) technique that rapidly identifies the type of caliber through analysis of the GSR would be an invaluable tool for a forensic investigator.

The chemical nature of GSR particles gives information about the gun, ammunition, and the shooting distance (and direction). GSR recovered at crime scenes is among the most important type of evidence to forensic investigators (Stich et al., "Raman Microscopic Identification of Gunshot Residues," *J. Raman Spectroscopy* 29(9):787-790 (1998)). The chemical composition of GSR is directly related to the chemical composition of the ammunition used. In addition, the chemical composition of GSR varies with the type of weapon since the latter determines specific conditions of the combustion process. Therefore, differences from ammunition to ammunition and, between different firearms will propagate to differences in the GSR. Conventional methods of GSR identification use labor-intensive, technologically diverse methods that are costly in terms of time and sample usage (Stich et al., "Raman Microscopic Identification of Gunshot Residues," *J. Raman Spectroscopy* 29(9):787-790 (1998)).

The objectives of any crime scene investigation are to preserve physical evidence and collect only valuable evidence for the analytical examination. The ability to characterize an unknown GSR at the scene of the crime without destruction or having to wait for laboratory results is, therefore a very critical step in crime scene investigation. GSR is often collected as forensic evidence to determine if a suspect has recently fired a weapon (Silva et al., "Gunshot Residues: Screening Analysis by Laser-Induced Breakdown Spectroscopy," *J. Brazilian Chem. Soc.* 20(10):1887-1894 (2009); Romolo and Margot, "Identification of Gunshot Residue: A Critical Review," *Forensic Sci. Int'l.*, 119:195-211 (2001); Garofano et al., "Gunshot Residue—Further Studies on Particles of Environmental and Occupational Origin," *Forensic Sci. Int'l.* 103(1):1-21 (1999); and Dockery and Goode, "Laser-Induced Breakdown Spectroscopy for the Detection of Gunshot Residues on the Hands of a Shooter," *Applied Optics* 42(30):6153-6158 (2003)), estimate the shooting distance (Santos et al., "Firing Distance Estimation Through the Analysis of the Gunshot Residue Deposit Pattern Around the Bullet Entrance Hole by Inductively Coupled Plasma-Mass Spectrometry—An Experimental Study," *Am. J. Forensic Med. Pathol.* 28(1):24-30 (2007); Capannesi et al., "Determination of Firing Distance and Firing Angle by Neutron Activation Analysis in a Case Involving Gunshot Wounds," *Forensic Sci. Int'l.* 61(2-3):75-84 (1993); Sharma and Lahiri, "A Preliminary Investigation Into the Use of FTIR Microscopy as a Probe for the Identification of Bullet Entrance Holes and the Distance of Firing," *Science & Justice* 49(3):197-204 (2009); Neri et al., "The Determination of Firing Distance Applying a Microscopic Quantitative Method and Confocal Laser Scanning Microscopy for Detection of Gunshot Residue Particles," *Int'l. J. Legal Med.* 121(4):287-292 (2007); and Brown et al., "Image Analysis of Gunshot Residue on Entry Wounds: II—A Statistical Estimation of Firing Range," *Forensic Sci. Int'l.* 100(3):179-186 (1999)) and confirm if a shooting has actually occurred.

Current methods for identifying GSR include the Modified Griess test, sodium rhodizonate test, gas-chromatography mass-spectrometry and scanning electron microscopy (SEM) combined with energy-dispersive X-ray analysis (EDX). Several of these methods require treating gunshot residue samples with reagents, including acids or other solvents, causing the methods to be destructive to the residue or other physical evidence involved with the sample. SEM/EDX is the preferred confirmatory test associated with GSR analysis (Stich et al., "Raman Microscopic Identification of Gunshot Residues," *J. Raman Spectroscopy* 29(9):787-790 (1998)). Unfortunately, this test requires relatively excessive amounts of time due to sampling procedures. Additionally, with the use of "lead-free" or "nontoxic" ammunitions, it is difficult to prevent false positives when searching for GSR by conventional SEM/EDX protocols (Burleson et al., "Forensic Analysis of a Single Particle of Partially Burnt Gunpowder by Solid Phase Micro-Extraction-Gas Chromatography-Nitrogen Phosphorus Detector," *J. Chromatography A* 1216(22):4679-4683 (2009)). Nevertheless, all of these methods test for the presence of GSR; but cannot identify and distinguish the type of caliber which produced the GSR recovered from the crime scene.

One conventional test for analyzing GSR is a chemical test, called the Modified Griess test. The Modified Griess test is a test to detect the presence of nitrite residues, and is the primary test used by firearms examiners to determine a muzzle-to-garment distance. The Modified Griess test is performed first on the GSR since the test will not interfere with later tests for lead residues. Nitrite residues are a byproduct of the combustion of smokeless gunpowder. When a gun is discharged, nitrite particles are expelled from the muzzle of a gun and can be imbedded in, or deposited on, the surface of a target. Another conventional test conducted on GSR is called the sodium rhodizonate test, which is a chemical test designed to determine if lead residues are present on the exhibit.

A problem with both the Modified Griess test and the sodium rhodizonate test is that most shooting cases involve firing at close range, and these tests are not applicable to shootings at close ranges (e.g., less than 5 feet). These techniques can only observe microscopic particles (particles whose diameter is a few microns or more) that are formed at distances of 5 feet or longer from the gun. Currently the GSR patterns are experimentally matched with the patterns at the crime scene on test firing. This is a time consuming and expensive process, and, again, does not work for short distances since it is difficult to observe a pattern in such a short distance. Moreover, these techniques require substantial amounts of GSR samples, which are difficult to obtain and are frequently contaminated. Accordingly, conventional techniques used for GSR analysis are limited, so prosecuting and defense attorneys typically rely on other evidence such as cartridge case volume and witness testimony to build a given case.

Several other analytical methods, including bulk and single particle analysis, are used to achieve GSR identification, but there is no standardized procedure to test for GSR. Single particle analysis combines chemical and morphological information to classify a suspected particle. The most widely accepted GSR analysis method is Scanning Electron Microscopy combined with Energy Dispersive X-Ray Spectroscopy (SEM/EDX). SEM/EDX is able to identify a sample as GSR based upon its ability to detect the elements mentioned previously in certain concentrations (Nesbitt et al., "Detection of Gunshot Residue by Use of the Scanning Electron Microscope," *J. Forensic Sci.* 21:595-610 (1976)). Unfortunately, this test is excessive in terms of time, sampling procedures, and instrumentation requirements. Since this technique relies heavily on the detection of lead, the removal of lead containing primers by manufacturers, citing health reasons, (Steffen et al., "Chemometric Classification of Gunshot Residues Based on Energy Dispersive X-ray Microanalysis and Inductively Coupled Plasma Analysis With Mass-Spectrometric Detection," *Spectrochimica Acta Part B-Atomic Spectroscopy* 62(9): 1028-1036 (2007)) has caused an increase in false positive results for SEM/EDX procedures (Burleson et al., "Forensic Analysis of a Single Particle of Partially Burnt Gunpowder by Solid Phase Micro-Extraction-Gas Chromatography-Nitrogen Phosphorus Detector," *J. Chromatog. A* 1216(22): 4679-4683 (2009)). Furthermore, SEM/EDX is unable to detect lighter elements (oxygen, carbon, and nitrogen) found in components of the primer and propellant (Schwoeble and Exline, *Current Methods in Forensic Gunshot Residue Analysis*. CRC Press:New York (2000)) and consequently provides limited analysis. Nevertheless, elemental analysis techniques are used as identification rather than chemical characterization methods and are destructive to forensic evidence.

Bulk methods are based upon qualitative detection of specific elements, usually heavy metals. Combinations of lead (Pb), barium (Ba), and antimony (Sb) are considered unique to GSR (Schwoeble and Exline, *Current Methods in Forensic Gunshot Residue Analysis*. CRC Press:New York (2000)) but also occur in environmental contaminants. Unfortunately, bulk methods often make conclusions based upon detection of these elements that are not necessarily generated by GSR. This leads to a lack of specificity for methods such as flameless atomic absorption (FAA) and neutron activation analysis (NAA) (Wallace and McQuillan, "Discharge Residues from Cartridge-operated Industrial Tools," *J. Forensic Sci. Soc.* 24(5):495-508 (1984)), which often misclassify environmental containments as being GSR.

Detection of these components provides several advantages over current elemental analysis techniques. For example, current techniques cannot distinguish whether detected lead originated from lead sulfate (a common primer component) or car battery acid. Therefore, the occupation of a suspect must be taken into account, because the source of the lead may not have originated from the discharging of a firearm. The method of the present invention offers a rapid, portable and sensitive alternative for GSR identification. Additionally, this technique will provide information about the original shooting parameters that can help link a suspect to a crime scene.

No existing technique is currently used to determine the type of ammunition and/or weapon type based upon GSR composition analysis. The forensic science community is in need of a technology that can (i) quickly identify the presence of GSR and (ii) match it to a specific type of ammunition and/or weapon type. The methods described in the present invention will fulfill these needs. The main advantage of the purposed technology over current GSR composition analysis is the ability to use the information to link the GSR to a specific ammunition and/or weapon type. Other advantages include the capacity to perform this technique in the field and in a relatively swift manner. Spectral collection at the crime scene and data analysis will be automated and will take very little time.

Accordingly, the present invention is directed to overcoming these deficiencies in the art.

SUMMARY OF THE INVENTION

One aspect of the present invention relates to a method of identifying ammunition type and/or weapon type used to fire the ammunition from gunshot residue (GSR). The method includes providing a sample which includes a gunshot residue, subjecting the sample to spectroscopic analysis to produce a spectroscopic signature for the sample, and identifying the spectroscopic signature to ascertain the type of ammunition and/or the type of weapon used to fire the ammunition.

Another aspect of the present invention is related to a method of establishing reference spectroscopic signatures for ammunition type and/or weapon type used to fire the ammunition. This method includes providing known samples comprising gunshot residues from known types of ammunition and/or types of weapons used to fire the ammunition, subjecting the known sample to spectroscopic analysis to produce a spectroscopic signature for each known sample, and establishing a reference spectroscopic signature for the type of ammunition and/or the type of weapon used to fire ammunition based on the spectroscopic signature obtained for each known sample subjected to spectroscopic analysis.

The present invention relates to characterizing the composition of GSR particles, identifying the specific size of ammunition (caliber) and/or the weapon type that was used to fire the ammunition. The methods of the present invention may involve the implementation of Raman microspectroscopy, which provides a broader chemical analysis (compared to current techniques) by detecting both organic and inorganic components of GSR in a nondestructive manor. By the very nature of Gunshot residue evidence, the amount of available sample is small, and the ability of Raman spectroscopy to obtain conclusive results from a very small amount is extremely valuable. Raman spectroscopy has several applications in forensic science, including identification of explosives (Ali et al., "In-situ Detection of Single Particles of Explosive on Clothing with Confocal Raman Microscopy," *Talanta* 78(3):1201-1203 (2009), which is hereby incorporated by reference in its entirety), paint (Suzuki and Carrabba, "In situ Identification and Analysis of Automotive Paint Pigments Using Line Segment Excitation Raman Spectroscopy: I. Inorganic Topcoat Pigments," *J. Forensic Sci.* 46(5):1053-1069 (2001), which is hereby incorporated by reference in its entirety), textile dyes (Abbott et al., "Resonance Raman and UV-Visible Spectroscopy of Black Dyes on Textiles," *Forensic Sci. Int'l.* 202(1-3):54-63 (2001), which is hereby incorporated by reference in its entirety), drugs (Hodges and Akhavan, "The Use of Fourier Transform Raman Spectroscopy in the Forensic Identification of Illicit Drugs and Explosives," *Spectrochimica Acta Part A: Molecular Spectroscopy* 46(2):303-307 (1990) and Ali et al., "In-situ Detection of Drugs-of-Abuse on Clothing Using Confocal Raman Microscopy," *Analytica Chimica Acta* 615(1):63-72 (2008), which are hereby incorporated by reference in their entirety) and body fluids (Virkler and Lednev, "Raman Spectroscopy Offers Great Potential for the Nondestructive Confirmatory Identification of Body Fluids," *Forensic Sci. Int'l.* 181(1-3):e1-e5 (2008), which is hereby incorporated by reference in its entirety). Additionally, Raman analysis of GSR has already been implemented by Stich et al. (Stich et al., "Raman Microscopic Identification of Gunshot Residues," *J. Raman Spectroscopy* 29(9):787-790 (1998), which is hereby incorporated by reference in its entirety), in which four different inorganic components (including barium, lead and iron compounds) of GSR were identified, with results consistent to SEM/EDX analysis.

The benefits of the present invention in the forensic community are significant. This invention illustrates that it is possible to discriminate between different types of ammunition by using Raman spectroscopy combined with advanced statistical analysis. Therefore, it is feasible to develop an easy-to-use (i) desktop instrument for laboratory use or (ii) portable instrument for on field applications for rapid analysis of GSR.

BRIEF DESCRIPTION OF THE DRAWINGS

FIG. 2A shows Raman spectra for .38 caliber ammunition. FIG. 2B shows Raman spectra for .40 caliber.

FIG. 4A shows PCA based hierarchical clustering for 0.38 caliber ammunition. FIG. 4B shows PCA based hierarchical clustering for 0.40 caliber ammunition. Clustering resulted in a grouping of Raman spectra into subsets, such that those within particular subset have higher degree of similarity to one another than Raman spectra assigned to different clusters.

FIG. 7A is a direct comparison of 0.38 and 0.40 data sets which reveals a strong fluorescent background for 35% of spectra collected from 0.38 caliber particles. FIG. 7B is PCA analysis of the raw Raman spectra which shows a good separation of this 35% fraction (red triangles "▼" outside of the dotted rectangle). FIG. 7C is PCA analysis of normalized, by area, spectra. The score plot shows that there are regions which are dominated only by one of two calibers. FIG. 7D shows that fluorescence does not correlate with the observed differentiation; the score plot in FIG. 7C was modified using a new coloring scheme. Blue squares and purple diamonds present the spectra falling inside and outside of the dotted rectangle in FIG. 7B.

DETAILED DESCRIPTION OF THE INVENTION

One aspect of the present invention relates to a method of identifying ammunition type and/or weapon type used to fire the ammunition from gunshot residue (GSR). The method includes providing a sample which includes a gunshot residue, subjecting the sample to spectroscopic analysis to produce a spectroscopic signature for the sample, and identifying the spectroscopic signature to ascertain the type of ammunition and/or the type of weapon used to fire the ammunition.

In the present invention, the term "spectroscopic signature" refers to a single spectrum, an averaged spectrum, multiple spectra, or any other spectroscopic representation of intrinsically heterogeneous samples of GSR.

Figure 1:
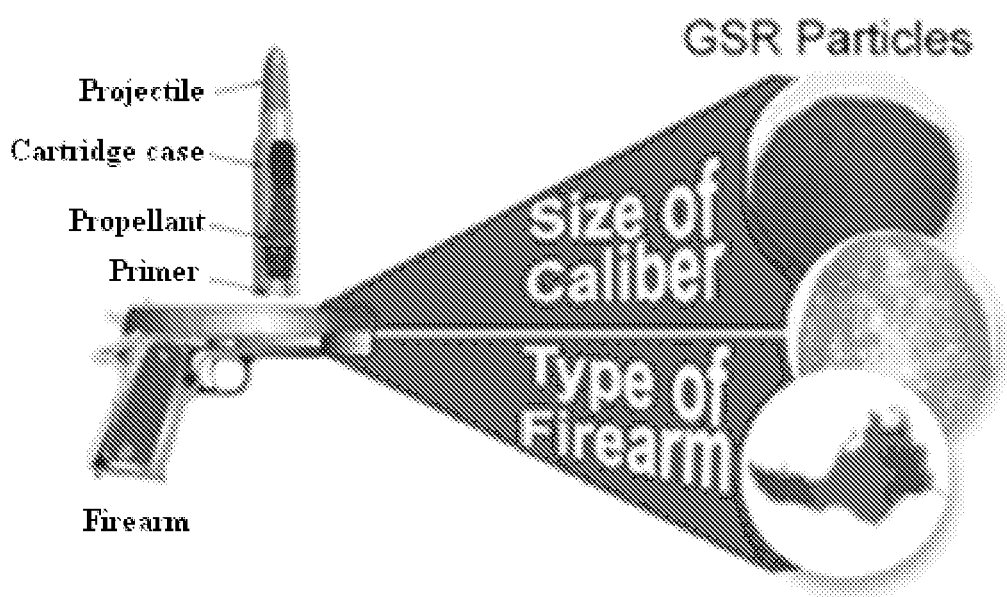
FIG. 1 relates to the formation of GSR. This could be considered a complex chemical process in which the product is determined by the reagents and the reaction conditions.

The aim of the present invention is to provide the ability to differentiate GSR particles generated with different shooting parameters. The firearm discharge process is analogous to a complex chemical reaction. As illustrated in FIG. 1, the reagents of this process are represented by the chemical composition of the ammunition, firearm and cartridge case, and GSR particles are the subsequent products. To emphasize, GSR particles hold specific chemical information about the ammunition and the firearm that was discharged. Over thirty five different organic compounds are present in propellant mixtures. Additionally, in excess of twenty inorganic complexes, consisting of over ten metallic elements, were reported as existing in primer mixtures (Dalby et al., "Analysis of Gunshot Residue and Associated Materials—A Review," *J. Forensic Sci.* 55(4):924-943 (2010), which is hereby incorporated by reference in its entirety). The concentration of these compounds in GSR depends on several factors, including the type, size, and age of the ammunition that was discharged. The conditions of the reaction are dependent upon the type and size of the firearm and ammunition as well as the firing mechanism used in the shooting incident.

The effect of caliber size and specific ammunition-weapon combinations on the chemical nature of GSR particles is the focus of the present invention. The size of the caliber (or the diameter of the ammunition cartridge and barrel of a firearm in hundredths of an inch) affects the level of combustion a GSR particle experiences as well as the size, shape, and color of the particle (Pun and Gallusser, "Macroscopic Observation of the Morphological Characteristics of the Ammunition Gunpowder," *Forensic Sci. Int'l.* 175(2-3):179-185 (2008), which is hereby incorporated by reference in its entirety). The size, density, and direction of the gaseous GSR discharge are also affected by caliber size (Schwoeble and Exline, *Current Methods in Forensic Gunshot Residue Analysis*. CRC Press:New York (2000), which is hereby incorporated by reference in its entirety). Changing one or more of these factors, changes the chemical nature of the resulting GSR particle. The present invention explores the variations in Raman spectra of GSR among the two particular firearm-ammunition combinations, with the purpose of identifying the firearm or caliber size used to produce the GSR. Raman analysis can identify components of GSR originating from both the propellant and the primer of the original ammunition (Sharma and Lahiri, "A Preliminary Investigation Into the Use of FTIR Microscopy as a Probe for the Identification of Bullet Entrance Holes and the Distance Of Firing," *Science & Justice* 49(3):197-204 (2009) and Stich et al., "Raman Microscopic Identification of Gunshot Residues," *J. Raman Spectroscopy* 29(9):787-790 (1998), which are hereby incorporated by reference in their entirety). Since the variation in the chemical composition of GSR with the type of ammunition and/or weapon is small, advanced statistical analysis is used for enhancing the differentiating power of the method.

The methods of the present invention are particularly suited to identify the type of ammunition used. The type of ammunition can be, for example, 9 mm caliber, .45 caliber, .40 caliber, .22 L caliber, and .38 Special.

The methods of the present invention can also be used to identify the type of weapon used to discharge the ammunition. The type of firearm can be, for example, Bersa Thunder 9, Glock Model 21, Smith and Wesson, Smith and Wesson 422, Smith and Wesson 40 revolver. However, this method may be applied for any firearm (or a tool that can be carried by an individual with the means of discharging a lethal projectile).

The method of the present invention further involve comparing the spectroscopic signature of a sample to reference spectroscopic signatures for different types of ammunition and/or types of weapons used to fire the ammunition. The type of ammunition and/or the type of weapon used to fire the ammunition can be characterized by comparing the spectroscopic signature of the sample to the reference spectroscopic signals. Training sets of GSR samples can be used to develop a set of latent variables (e.g., multi-dimensional spectroscopic signatures), which will be sufficient for a confident differentiation. In other words, the clusters of points calculated for different ammunition types/weapon types using the latent variables should be separated with sufficient confident interval in the multi-dimensional score space and can be used for the purposes of the present invention.

Another aspect of the present invention is related to a method of establishing reference spectroscopic signatures for ammunition type and/or weapon type used to fire the ammunition. This method includes providing known samples comprising gunshot residues from known types of ammunition and/or types of weapons used to fire the ammunition, subjecting the known sample to spectroscopic analysis to produce a spectroscopic signature for each known sample, and establishing a reference spectroscopic signature for the type of ammunition and/or the type of weapon used to fire ammunition based on the spectroscopic signature obtained for each known sample subjected to spectroscopic analysis.

The reference spectroscopic signatures can be established for various types of ammunition. Similarly, the reference spectroscopic signatures can be established for various types of weapons used to fire the ammunition.

Raman spectroscopy is a spectroscopic technique which relies on inelastic or Raman scattering of monochromatic light to study vibrational, rotational, and other low-frequency modes in a system (Gardiner, D. J., *Practical Raman Spectroscopy*, Berlin: Springer-Verlag, pp. 1-3 (1989), which is hereby incorporated by reference in its entirety). Vibrational modes are very important and very specific for chemical bonds in molecules. They provide a fingerprint by which a molecule can be identified. The Raman effect is obtained when a photon interacts with the electron cloud of a molecular bond exciting the electrons into a virtual state. The scattered photon is shifted to lower frequencies (Stokes process) or higher frequencies (anti-Stokes process) as it abstracts or releases energy from the molecule. The polarizability change in the molecule will determine the Raman scattering intensity, while the Raman shift will be equal to the vibrational intensity involved.

Raman spectroscopy is based upon the inelastic scattering of photons or the Raman shift (change in energy) caused by molecules. The analyte is excited by laser light and upon relaxation scatters radiation at a different frequency which is collected and measured. With the availability of portable Raman spectrometers it is possible to collect Raman spectra in the field. Using portable Raman spectrometers offers distinct advantages to government agencies, first responders and forensic scientists (Hargreaves et al., "Analysis of Seized Drugs Using Portable Raman Spectroscopy in an Airport Environment—a Proof of Principle Study," *J. Raman Spectroscopy* 39(7):873-880 (2008), which is hereby incorporated by reference in its entirety). Stich, et al. identified several components of GSR particles via Raman spectrometry with results consistent to SEM/EDX analysis (Stich et al., "Raman Microscopic Identification of Gunshot Residues," *J. Raman Spectroscopy* 29(9):787-790 (1998), which is hereby incorporated by reference in its entirety). Conclusions from their experiment illustrate that Raman spectrometry is able to contribute in a swift and cost effective way to the armory of the modern forensic science laboratory.

Raman spectroscopy is increasing in popularity among the different disciplines of forensic science. Some examples of its use today involve the identification of drugs (Hodges et al., "The Use of Fourier Transform Raman Spectroscopy in the Forensic Identification of Illicit Drugs and Explosives," *Molecular Spectroscopy* 46:303-307 (1990), which is hereby incorporated by reference in its entirety), lipsticks (Rodger et al., "The In-Situ Analysis of Lipsticks by Surface Enhanced Resonance Raman Scattering," *Analyst* 1823-1826 (1998), which is hereby incorporated by reference in its entirety), and fibers (Thomas et al., "Raman Spectroscopy and the Forensic Analysis of Black/Grey and Blue Cotton Fibers Part 1: Investigation of the Effects of Varying Laser Wavelength," *Forensic Sci. Int.* 152:189-197 (2005), which is hereby incorporated by reference in its entirety), as well as paint (Suzuki et al., "In Situ Identification and Analysis of Automotive Paint Pigments Using Line Segment Excitation Raman Spectroscopy: I. Inorganic Topcoat Pigments," *J. Forensic Sci.* 46:1053-1069 (2001), which is hereby incorporated by reference in its entirety) and ink (Mazzella et al., "Raman Spectroscopy of Blue Gel Pen Inks," *Forensic Sci. Int.* 152:241-247 (2005), which is hereby incorporated by reference in its entirety) analysis. Very little or no sample preparation is needed, and the required amount of tested material could be as low as several picograms or femtoliters ($10^{-12}$ gram or $10^{-15}$ liter, respectively). A typical Raman spectrum consists of several narrow bands and provides a unique vibrational signature of the material (Grasselli et al., "Chemical Applications of Raman Spectroscopy," New York: John Wiley & Sons (1981), which is hereby incorporated by reference in its entirety). Unlike infrared (IR) absorption spectroscopy, another type of vibrational spectroscopy, Raman spectroscopy shows very little interference from water (Grasselli et al., "Chemical Applications of Raman Spectroscopy," New York: John Wiley & Sons (1981), which is hereby incorporated by reference in its entirety), and that makes it a great technique for analyzing GSR and their traces. Proper Raman spectroscopic measurements do not damage the sample. A swab could be tested on the field and still be available for further use in the lab, and that is very important to forensic application. The design of a portable Raman spectrometer is a reality now (Yan et al., "Surface-Enhanced Raman Scattering Detection of Chemical and Biological Agents Using a Portable Raman Integrated Tunable Sensor," *Sensors and Actuators B*. 6 (2007); Eckenrode et al., "Portable Raman Spectroscopy Systems for Field Analysis," *Forensic Science Communications* 3:(2001), which are hereby incorporated by reference in their entirety) which would lead to the ability to make identifications at the crime scene.

Fluorescence interference is the largest problem with Raman spectroscopy and is perhaps the reason why the latter technique has not been more popular in the past. If a sample contains molecules that fluoresce, the broad and much more intense fluorescence peak will mask the sharp Raman peaks of the sample. There are a few remedies to this problem. One solution is to use deep ultraviolet (DUV) light for exciting Raman scattering (Lednev I. K., "Vibrational Spectroscopy: Biological Applications of Ultraviolet Raman Spectroscopy," in: V. N. Uversky, and E. A. Permyakov, *Protein Structures, Methods in Protein Structures and Stability Analysis* (2007), which is hereby incorporated by reference in its entirety). Practically no condensed face exhibits fluorescence below ~250 nm. Possible photodegradation of biological samples is an expected disadvantage of DUV Raman spectroscopy. Another option to eliminate fluorescence interference is to use a near-IR (NIR) excitation for Raman spectroscopic measurement. Finally, surface enhanced Raman spectroscopy (SERS) which involves a rough metal surface can also alleviate the problem of fluorescence (Thomas et al., "Raman Spectroscopy and the Forensic Analysis of Black/Grey and Blue Cotton Fibers Part 1: Investigation of the Effects of Varying Laser Wavelength," *Forensic Sci. Int.* 152:189-197 (2005), which is hereby incorporated by reference in its entirety). However, this method requires direct contact with the analyte and cannot be considered to be nondestructive.

Basic components of a Raman spectrometer are (i) an excitation source; (ii) optics for sample illumination; (iii) a single, double, or triple monochromator; and (iv) a signal processing system consisting of a detector, an amplifier, and an output device.

Typically, a sample is exposed to a monochromatic source usually a laser in the visible, near infrared, or near ultraviolet range. The scattered light is collected using a lens and is focused at the entrance slit of a monochromator. The monochromator which is set for a desirable spectral resolution rejects the stray light in addition to dispersing incoming radiation. The light leaving the exit slit of the monochromator is collected and focused on a detector (such as a photodiode arrays (PDA), a photomultiplier (PMT), or charge-coupled device (CCD)). This optical signal is converted to an electrical signal within the detector. The incident signal is stored in computer memory for each predetermined frequency interval. A plot of the signal intensity as a function of its frequency difference (usually in units of wavenumbers, $cm^{-1}$) will constitute the Raman spectroscopic signature.

Raman signatures are sharp and narrow peaks observed on a Raman spectrum. These peaks are located on both sides of the excitation laser line (Stoke and anti-Stoke lines). Generally, only the Stokes region is used for comparison (the anti-Stoke region is identical in pattern, but much less intense) with a Raman spectrum of a known sample. A visual comparison of these set of peaks (spectroscopic signatures) between experimental and known samples is needed to verify the reproducibility of the data. Therefore, establishing correlations between experimental and known data is required to assign the peaks in the molecules, and identify a specific component in the sample.

The types of Raman spectroscopy suitable for use in conjunction with the present invention include, but are not limited to, conventional Raman spectroscopy, Raman microspectroscopy, near-field Raman spectroscopy, including but not limited to the tip-enhanced Raman spectroscopy, surface enhanced Raman spectroscopy (SERS), surface enhanced resonance Raman spectroscopy (SERRS), and coherent anti-Stokes Raman spectroscopy (CARS). Also, both Stokes and anti-Stokes Raman spectroscopy could be used.

In the present invention Raman microspectroscopy is combined with advanced statistical analysis to characterize and statistically differentiate GSR particles originating from different calibers. GSR particles from 0.38 and 0.40 caliber ammunitions were collected under identical conditions and analyzed by Raman microspectroscopy with a 406.7 nm excitation. Resulting spectra were pre-treated and advanced statistical methods including principle component analysis (PCA) and support vector machines (SMV) were used to differentiate the samples. PCA is a mathematical procedure which describes the most of spectral data variation using a smaller number of principle spectra (components) (Shashilov et al., "Advanced Statistical and Numerical Methods for Spectroscopic Characterization of Protein Structural Evolution," *Chem Rev.* 110(10):5692-5713 (2010), which is hereby incorporated by reference in its entirety). Such representation is used for the exploratory data analysis and for making predictive models. SVM is an extremely efficient classification method which is able to handle a strong fluorescent background variation, overlapping spectral bands, nonlinearity in spectral response due to absorbing components and molecular interactions between components, sample matrix effect (Franke, J. E., "Inverse Least Squares and Classical Least Squares Methods for Quantitative Vibrational Spectroscopy," In Chalmers, eds., *Handbook of Vibrational Spectroscopy*, Vol. 3, New York: John Whiley & Sons, Ltd., pp. 2276-2292 (2001), which is hereby incorporated by reference in its entirety). Leave-one-out cross validation reveals the exhaustiveness of the caliber identification. Results illustrate that the proposed method has great potential for differentiating crime scene GSR samples originating from different ammunition caliber and/or firearm combinations. This method should have a significant impact on the efficiency of crime scene investigations. One benefit of applying Raman spectroscopy to Gunshot residue is the ability to confirm the ammunition type and/or weapon type with one quick and simple analysis. Ultimately, the ability to perform this analysis at the scene of a crime will allow investigators to conclusively identify and/or confirm the ammunition type and/or weapon type. This will save time both on site and in the laboratory since further identification will not be necessary.

Other types of spectroscopic analysis are also proficient methods for detecting chemical composition differences between GSR samples. In addition to Raman spectroscopy, the spectroscopic analysis of the present invention can be performed using, for example, mass spectrometry, fluorescence spectroscopy, laser induced breakdown spectroscopy, infrared spectroscopy, scanning electron microscopy, X-ray diffraction spectroscopy, powder diffraction spectroscopy, X-ray luminescence spectroscopy, inductively coupled plasma mass spectrometry, capillary electrophoresis, or atomic absorption spectroscopy. Some of the spectroscopic methods mentioned above, including but not limited to Raman spectroscopy, are relatively simple, rapid, non-destructive, and would allow for the development of a portable instrument. The technique can be performed with relatively small samples, picogram (pg) quantities. The composition of the sample is not changed in any way, allowing for further forensic tests on the residue or other components of the evidence. The methods of the present invention do not require any sophisticated instrumentation or any sample preparation.

Scanning Electron Microscopy combined with Energy Dispersive Spectroscopy (SEM/EDS or EDX when equipped with an X-ray analyzer) is capable of obtaining both morphological information and the elemental composition of GSR particles. Recently, SEM/EDS systems have become automated, making automated computer-controlled SEM the method of choice for most laboratories conducting GSR analyses. Several features of the SEM make it useful in many forensic studies, and especially in GSR analysis, including magnification, imaging, composition analysis, and automation (Schwoeble and Exline, "Current Methods in Forensic Gunshot Residue Analysis," CRC Press: New York (2000), which is hereby incorporated by reference in its entirety).

Inductively coupled plasma mass spectrometry (ICP-MS) is a mass analysis method with sensitivity to metals. As a result, this analytical technique is ideal for analyzing barium, lead, and antimony, the major elements commonly found in GSR (Sarkis et al., "Measurements of Gunshot Residues by Sector Field Inductively Coupled Plasma Mass Spectrometry—Further Studies With Pistols," *Forensic Science International* 172(1):63-66 (2007), which is hereby incorporated by reference in its entirety). This technique is known for its sensitivity, having detection limits that are usually in the parts per billion (Schwoeble and Exline, "Current Methods in Forensic Gunshot Residue Analysis," CRC Press: New York (2000), which is hereby incorporated by reference in its entirety). ICP-MS has proven to be a fast, precise, and trustworthy analytical method for the confirmation of firearm discharge (Sarkis et al., "Measurements of Gunshot Residues by Sector Field Inductively Coupled Plasma Mass Spectrometry—Further Studies with Pistols," *Forensic Science International* 172(1):63-66 (2007), which is hereby incorporated by reference in its entirety).

Fourier transform infrared (FTIR) spectroscopy is a versatile tool for the detection, estimation and structural determination of organic compounds such as drugs, explosives, and organic components of GSR. FTIR can be utilized for the detection of organic gunshot residue (OGSR) at the bullet entrance hole and on the hands and clothing of the shooter. Furthermore, FTIR shows promise in its ability to determine the shooting distance (Sharma and Lahiri, "A Preliminary Investigation into the Use of FTIR Microscopy as a Probe for the Identification of Bullet Entrance Holes and the Distance of Firing," *Science & Justice* 49(3):197-204 (2009), which is hereby incorporated by reference in its entirety). Due to the availability of portable IR spectrometers, it will be possible to analyze OGSR at the crime scene. Capillary electrophoresis (CE) is another analytical technique that is applied to OGSR analysis. The significant advantage of CE is the low probability of false positives (Bell, S., *Forensic Chemistry*, Pearson Education: Upper Saddle River, N.J. (2006), which is hereby incorporated by reference in its entirety).

Atomic absorption spectroscopy (AAS) is a bulk method of analysis used in the analysis of inorganic materials in primer residue, namely Ba and Sb (Schwoeble and Exline, "Current Methods in Forensic Gunshot Residue Analysis," CRC Press: New York (2000), which is hereby incorporated by reference in its entirety). The high sensitivity for a small volume of sample is one advantage of AAS. This technique involves the absorption of thermal energy by the sample and subsequent emission of some or all of the energy in the form of radiation (Bauer et al., *Instrumental Analysis*, Allyn and Bacon, Inc.: Boston (1978), which is hereby incorporated by reference in its entirety). These emissions are generally unique for specific elements and thus give information about the composition of the sample. The determination of GSR residue by AAS has been used to measure the distribution of GSR particles (Stich et al., "Raman Microscopic Identification of Gunshot Residues," *J. Raman Spectroscopy* 29(9): 787-790 (1998), which is hereby incorporated by reference in its entirety). Laser-induced breakdown spectroscopy (LIBS) is a type of atomic emission spectroscopy that implements lasers to excite the sample. Rather than flame AAS, LIBS is accessible to field testing because of the availability of portable LIBS systems.

X-ray diffraction (XRD) is one such technique that can be used for the characterization of a wide variety of substances of forensic interest, including GSR (Abraham et al., "Application of X-Ray Diffraction Techniques in Forensic Science," *Forensic Science Communications* 9(2) (2007), which is hereby incorporated by reference in its entirety). XRD is capable of obtaining information about the actual structure of GSR samples, in a non-destructive manor.

EXAMPLES

The Examples set forth below are for illustrative purposes only and are not intended to limit, in any way, the scope of the present invention.

Example 1

Materials and Methods

9"×9" low lint cloth wipes obtained from Scientific Instrument Services, Inc. were used as the substrate to collect the discharged GSR. The cloth wipes were stapled to a cardboard back stop and hung approximately chest high. The cloth substrate was placed in front of the barrel of the firearm at a distance of one foot. This shooting distance was selected in order to maximize the number of GSR particles obtained. The procedure was repeated five times for a Smith and Wesson Model 10 Revolver with "0.38 special" ammunition and a Smith and Wesson M&P40 firearm with 0.40 cal full metal jacket ammunition which were used to generate the 0.38 and 0.40 caliber samples as listed in Table 1. All collections were preformed with the supervision and support of the New York State Police. GSR particles were removed from the cloth substrates, and placed on a plastic disc for analysis under a Renishaw inVia confocal Raman microscope equipped with a research grade Leica microscope, 50× objective, and WiRE 2.0 software. Several spectra were collected from different spots on the same GSR particle to take into account their heterogeneity. Therefore, each GSR particle was represented by a multispectral data set. Each single spectrum was an average of 5 scans for 35 s over a range of 200-3200 $cm^{-1}$. The excitation at 406.7 nm originated from a krypton ion laser (Coherent) with a laser power of approximately 10% relative to maximum (50 mW). The spectrometer was calibrated before Raman spectra collections with a silicon reference (520 $cm^{-1}$). All measurements were preformed under identical conditions using charge-coupled device camera (CCD), and representative raw spectra are illustrated in FIGS. 2A-B and FIG. 7A. Twenty spectra were collected for each firearm discharge sample (resulting in a total of 100 spectra per caliber). The cosmic ray contribution was removed from all Raman spectra using GRAMS/AI software package. The spectra were imported into MATLAB 7.9.0 for preprocessing and statistical analysis.

TABLE 1

Weapons and Ammunitions Used

| Weapon | Ammunition |
|---|---|
| Smith and Wesson M&P40 | .40 cal, Full Metal Jacket |
| Smith and Wesson Model 10 Revolver | .38 Special |

Example 2

Analysis of Spectra

Figure 2:
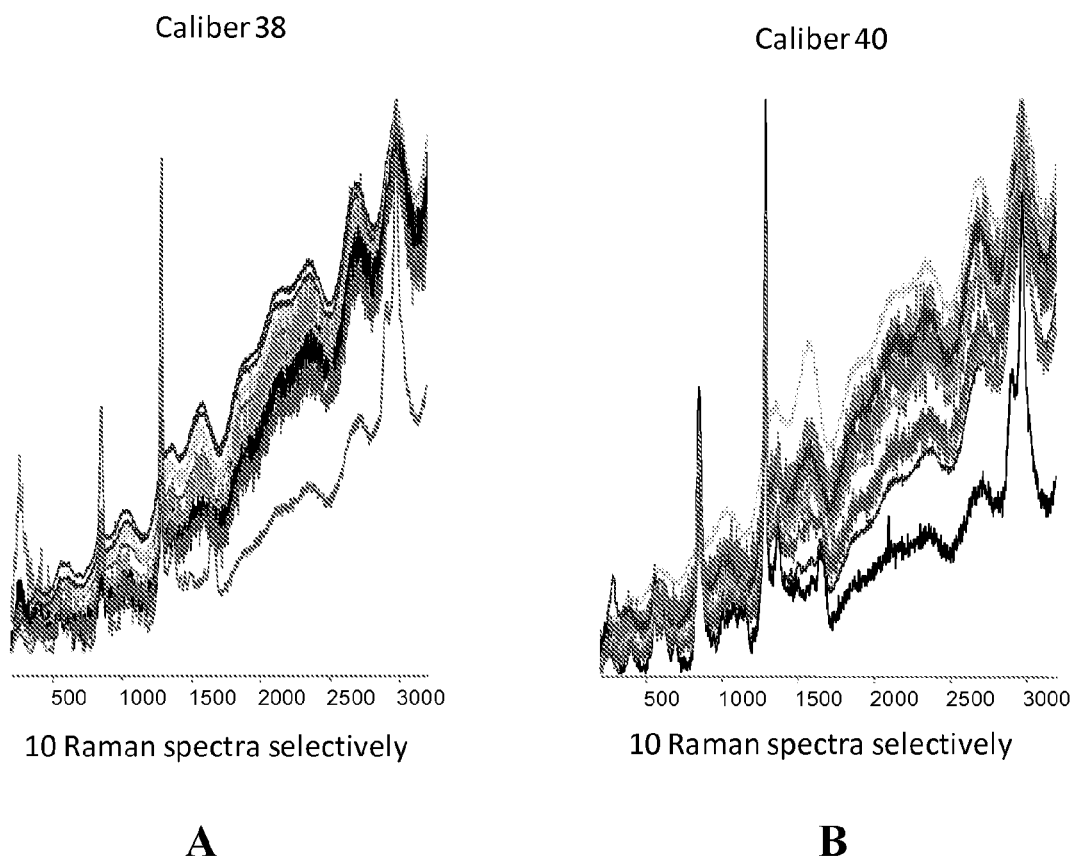
FIGS. 2A-B show raw Raman spectra of several GSR particles.
Figure 3:
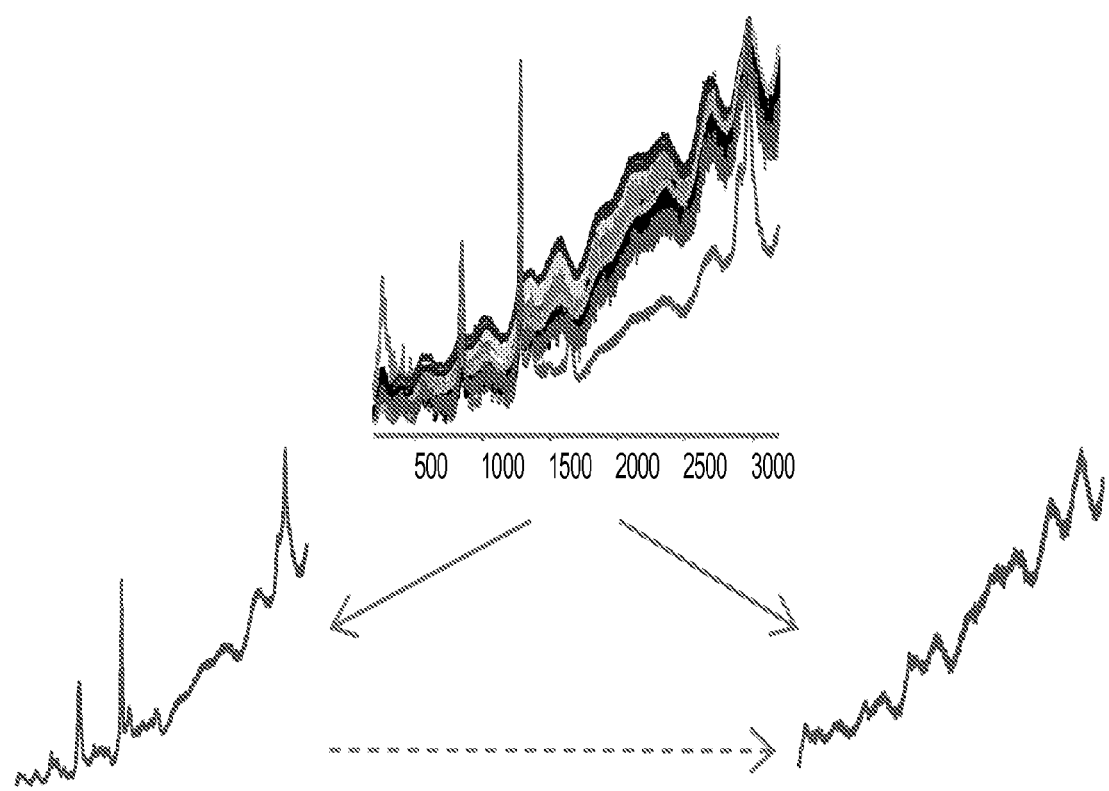
FIG. 3 shows two characteristic types of GSR Raman spectral profiles. Raman spectra with the more developed shape (multiple sharp Raman bands) potentially contain more information about GSR composition. Treatment of these spectra separately can be used to increase the efficiency of the caliber identification.

The Raman spectra of several GSR particles are shown in FIG. 2. Both .38 (FIG. 2A) and .40 (FIG. 2B) caliber data sets consist of two groups with similar spectral profiles (FIG. 3). The first group were formed by Raman spectra with wide Raman bands (FIG. 3, right side), while Raman spectra from the second group, in addition to the already mentioned wide peaks, have variable contribution of more narrow, and, probably, more specific, bands. The first group of .38 and .40 caliber spectra have similar shape and, as it was determined by different discriminant analysis (DA) techniques (Shashilov et al., "Advanced Statistical and Numerical Methods for Spectroscopic Characterization of Protein Structural Evolution," *Chem Rev.* 110(10):5692-5713 (2010); Wise et al., "PLS Toolbox 3.5 for Use with Matlab.," Vol. 17, Eigenvector Research Inc:Manson, Wash. (2005); *Chemometrics in Spectroscopy*, Mark et al., Elsevier (2007); *Chemometrics: From Basics to Wavelet Transformation*, Chau et al., Hoboken, N.J.:John Wiley & Sons, Inc, (2004), which are hereby incorporated by reference in their entirety) do not exhibit any unique information useful for caliber identification.

Figure 4:
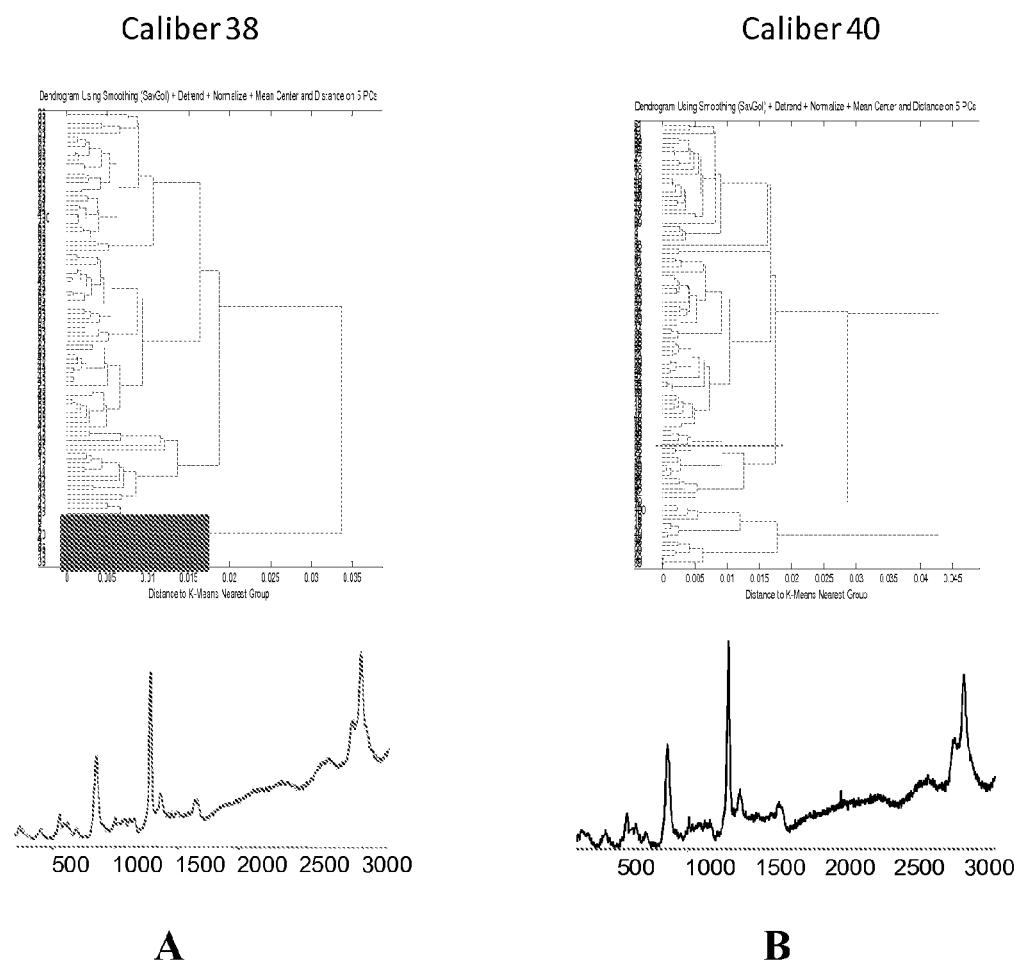
FIGS. 4A-B show Principal Component Analysis (PCA) based hierarchical clustering.

The second group of spectra is very inhomogeneous and includes spectra with intense, narrow Raman bands and high signal-to-noise ratio. Since it was assumed that it was possible to identify calibers using the unknown variable species, spectra with the higher evidence of this component were chosen from both calibers. Selection was done by PCA based hierarchical clustering (FIG. 4). (Shashilov et al., "Advanced Statistical and Numerical Methods for Spectroscopic Characterization of Protein Structural Evolution," *Chem Rev.* 110(10):5692-5713 (2010); Wise et al., "PLS Toolbox 3.5 for Use with Matlab.," Vol. 17, Eigenvector Research Inc:Manson, Wash. (2005), which are hereby incorporated by reference in their entirety).

Figure 5A:
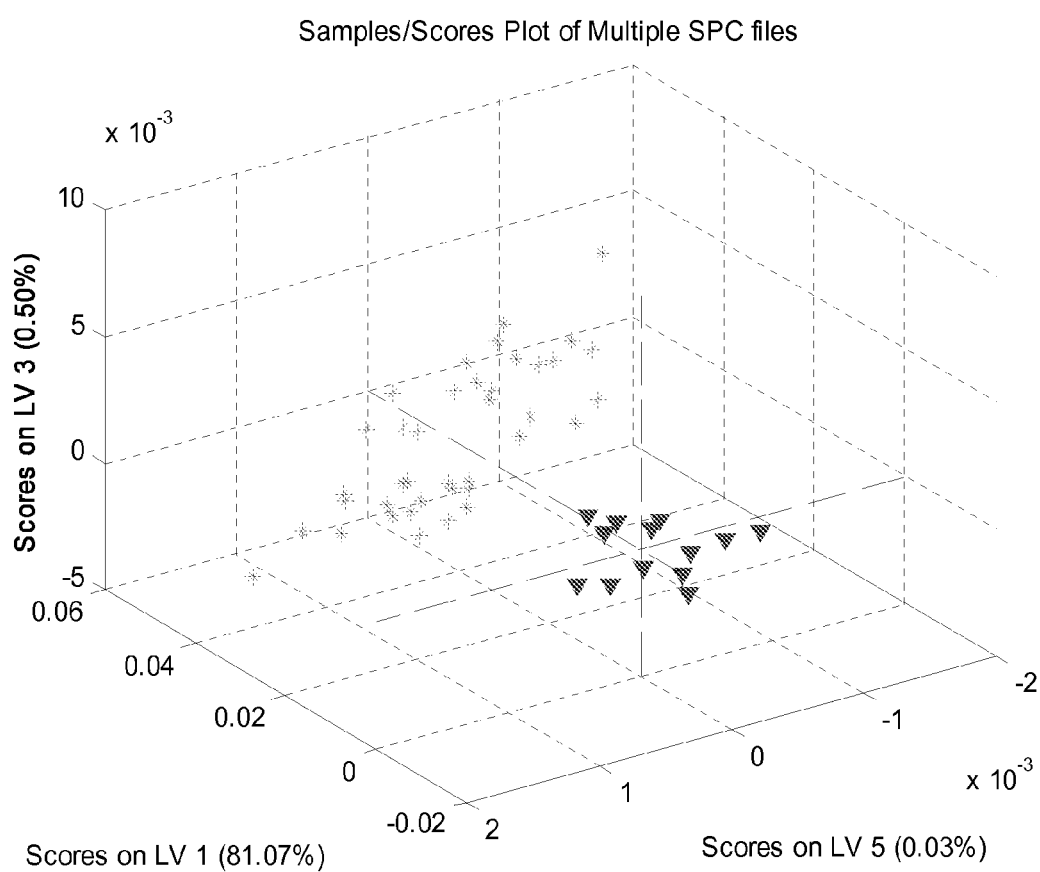
FIGS. 5A-B show grouping of the Raman spectra acquired from 0.38 and 0.40 calibers based upon three dimensional scores plot.
Figure 5B:
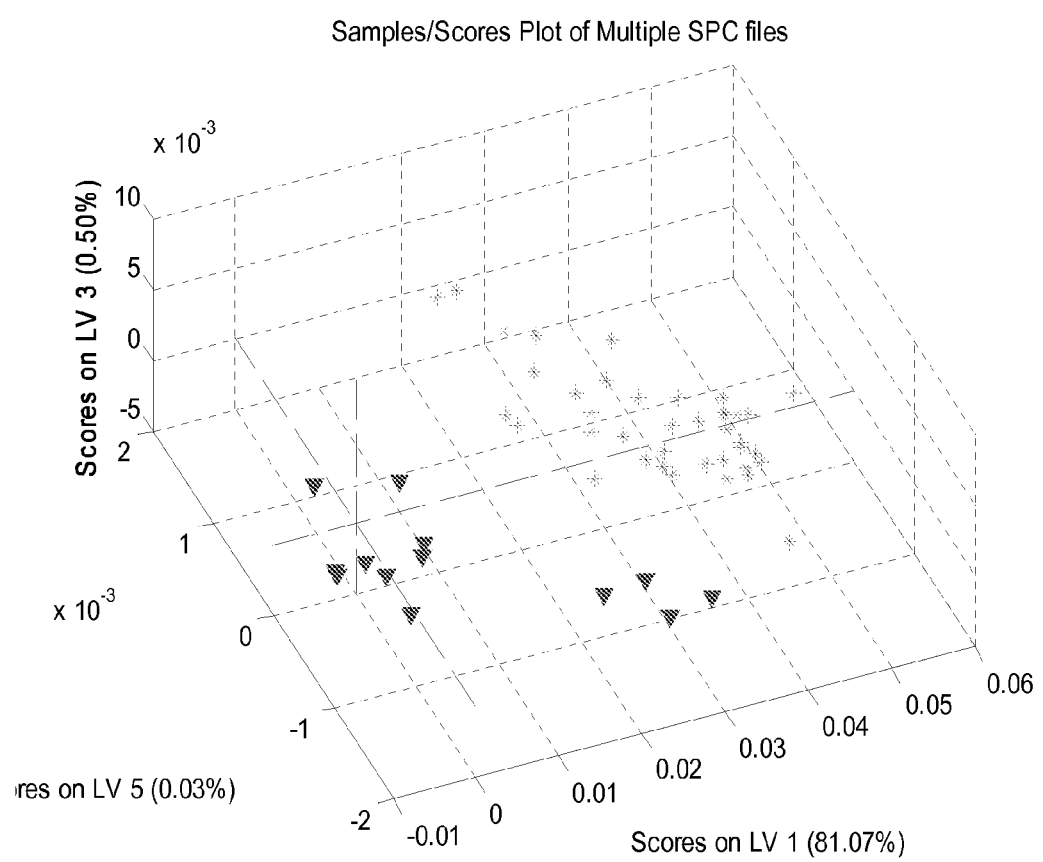

Raman spectra of these clusters were combined, defined as a separate class, and subjected to discriminant analysis by PLS-DA technique (Shashilov et al., "Advanced Statistical and Numerical Methods for Spectroscopic Characterization of Protein Structural Evolution," *Chem Rev.* 110(10):5692-5713 (2010); Wise et al., "PLS Toolbox 3.5 for Use with Matlab.," Vol. 17, Eigenvector Research Inc:Manson, Wash. (2005), which are hereby incorporated by reference in their entirety) together with the rest of .38 and .40 sets spectra. The processed .38 and .40 caliber data were entered into a three-dimensional scores plot as shown in FIGS. 5A and 5B. Clearly the differentiation between the calibers (.38 and .40) is illustrated. Results of analysis (FIG. 5) demonstrated that PLS-DA is able to discriminate spectra with narrow Raman bands from the raw data sets. Fitting in to the built model (this model is called a selection model) can be used as criterion for spectra selection. Therefore, determination of caliber is possible with this method.

Figure 5C:
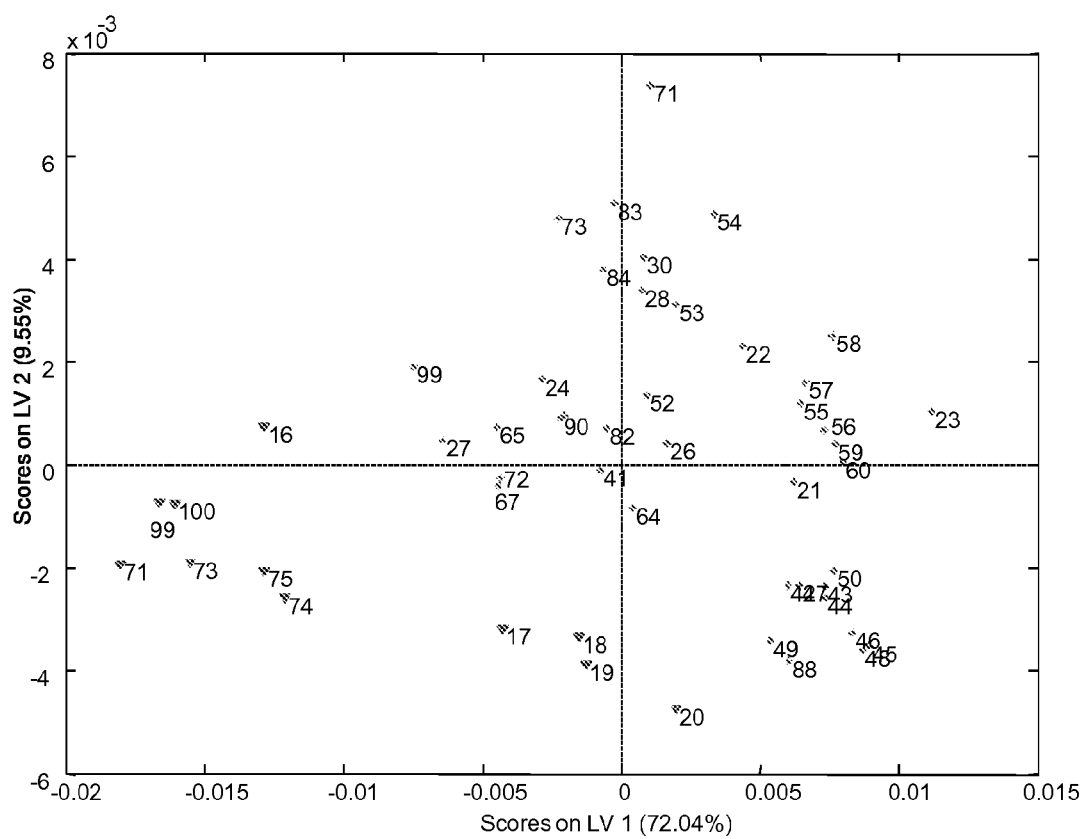
FIG. 5C shows the correlation between spectra and shot specific sample. Asterix ("*") denotes 0.40 caliber data and triangle ("▼") denotes 0.38 caliber data.

Spectra selected by PLS-DA selection were grouped in two new sets according to calibers. As a result, the same sets of Raman spectra were obtained, but now with the noninformative part extracted. Smoothing, baseline subtraction, normalization, and mean centering of the selected spectra were performed. For each caliber, the number of latent variables was calculated using contiguous block, leave-one-out, Venetian blind, and random subset cross-validation methods. Latent variables were used to create three-dimensional plots of the species in space in order to determine if each species would cluster and separate from the other species (FIG. 5). Two different projections of latent variables were chosen to show clustering and separation. FIG. 5 shows a three-dimensional view based on the first, third, and fifth latent variables. As mentioned previously, five different shots (samples) were collected from each caliber. A close examination of the Raman spectra distribution in the score space revealed strong correlation between subclusters and certain shot samples. Thus, for example, .38 spectra were forced into two subclusters. First subcluster is composed of spectra obtained from the shot number 1 (spectral indexes are 17-20), second subclass is a compilation of the certain spectra from the different shots (shot 1—spectral index 16, shot 4—spectral indexes 71,73-75, shot 5—spectral indexes 99-100). Also it is noted that distance between .38 caliber subclasses is comparable with the distance between the calibers. Outlined above are observations together with number labels which correlate the spectra to a specific sample (FIG. 5C). New Raman spectra collected from the same shots have, months after the first experiments, significantly lower intensity of the narrow peaks. All new spectra were not able to pass model-based selection. Lowering intensity may reflect instability of the chemical species (moisture, oxygen, sublimation). Time dependence may complicate analysis. It also provides the opportunity to obtain by Raman spectroscopy even more comprehensive forensic information such as the age of the GSR. In order to understand these changes, it may be important to test GSR samples under certain varying conditions, such as time and other environmental factors.

Figure 6:
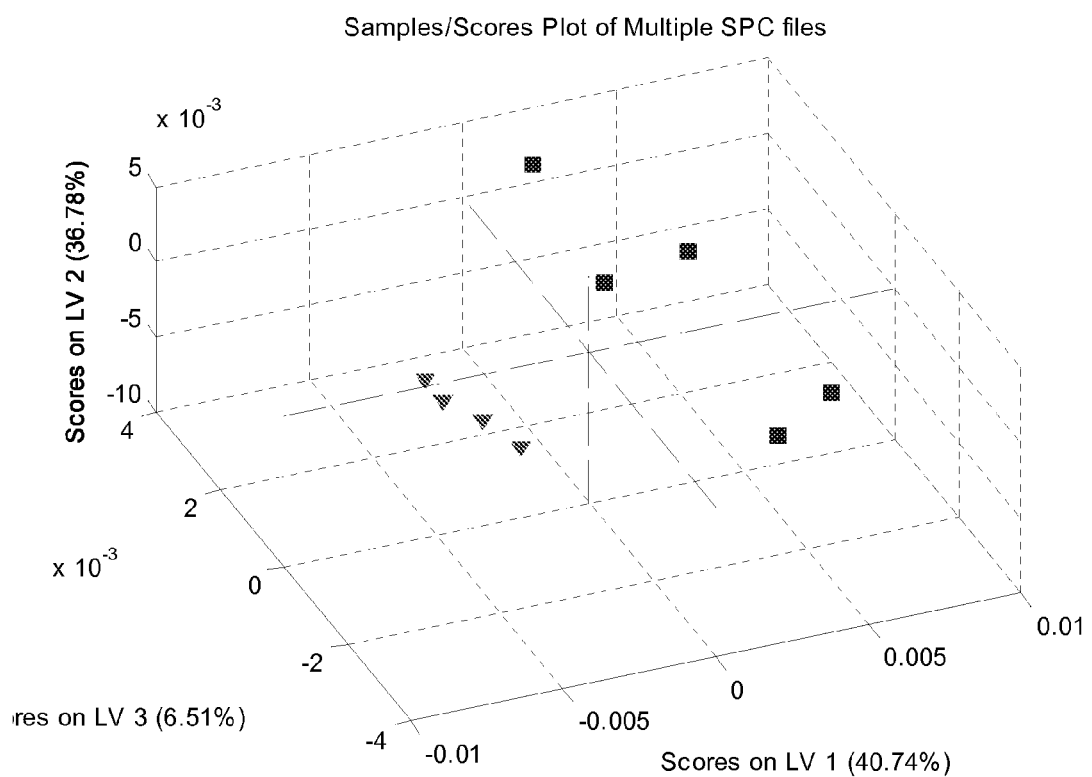
FIG. 6 shows grouping of the Raman spectra acquired from 0.38 and 0.40 calibers based upon three dimensional scores plot calculated using manually treated Raman spectra. Manual treatment includes but is not limited to spectra selection, baseline subtraction and cosmic rays removal.

Results obtained were generated by using automatic selection and pretreatment of spectra, including baseline subtraction, normalization, and mean centering. The automatic method is more favorable than the manual data treatment, because it requires less time by the analyst. An automated technique that is reproducible over a large scale of data would be an exciting result. Nevertheless, manual data treatment is possible (FIG. 6) and produces separation greater than or equal to the automatic technique.

The ability to provide evidence based on analysis of GSR has been one of the most consistent goals of forensic scientists since the turn of the century. Historically, GSR analysis has been used in criminal cases to estimate firing distance, indentify bullet holes, and determine whether or not a person has discharged a firearm (Meng and Caddy, "Gunshot Residue Analysis—A Review," *J. Forensic Sciences* 42(4):553-570 (1997), which is hereby incorporated by reference in its entirety). A nondestructive, confirmatory method of caliber identification via GSR analysis would be considered an innovative technique that most crime labs and military organizations would covet. The experimental procedure includes probing of GSR by Raman microscopy with 406.7 nm excitation. Discriminant Analysis (DA) (Shashilov et al., "Advanced Statistical and Numerical Methods for Spectroscopic Characterization of Protein Structural Evolution," *Chem Rev.* 110(10):5692-5713 (2010); Wise et al., "PLS Toolbox 3.5 for Use with Matlab.," Vol. 17, Eigenvector Research Inc:Manson, Wash. (2005), which are hereby incorporated by reference in their entirety), using PLS-DA techniques of .38 and .40 Raman spectra acquired under controlled laboratory conditions showed that calibers can be identified with good quality. Several different spectra preprocessing approaches were tested. Baseline subtraction, normalization and mean centering of Raman spectra significantly enhanced discrimination by the PLS-DA algorithm. Prior spectra selection was needed to eliminate nonspecific contribution. Significant factor analysis used for determining the number of latent variables was necessary and sufficient for PLS-DA model building. Three-dimensional score plots (FIG. 5), demonstrated clustering among .38 caliber.

Overall, Raman spectroscopy coupled with discriminant statistical analysis showed great potential for confirmatory identification of calibers at a crime scene. Together with other GSR analysis techniques, including mass spectrometry, fluorescence spectroscopy, laser induced breakdown spectroscopy, infrared spectroscopy, scanning electron microscopy, X-ray diffraction spectroscopy, powder diffraction spectroscopy, X-ray luminescence spectroscopy, inductively coupled plasma mass spectrometry, capillary electrophoresis, and atomic absorption spectroscopy, caliber identification will be possible. The ability to make these determinations and identifications, especially on-site at a crime scene, would be a major advance in the area of forensic GSR analysis.

Example 3

Figure 7:
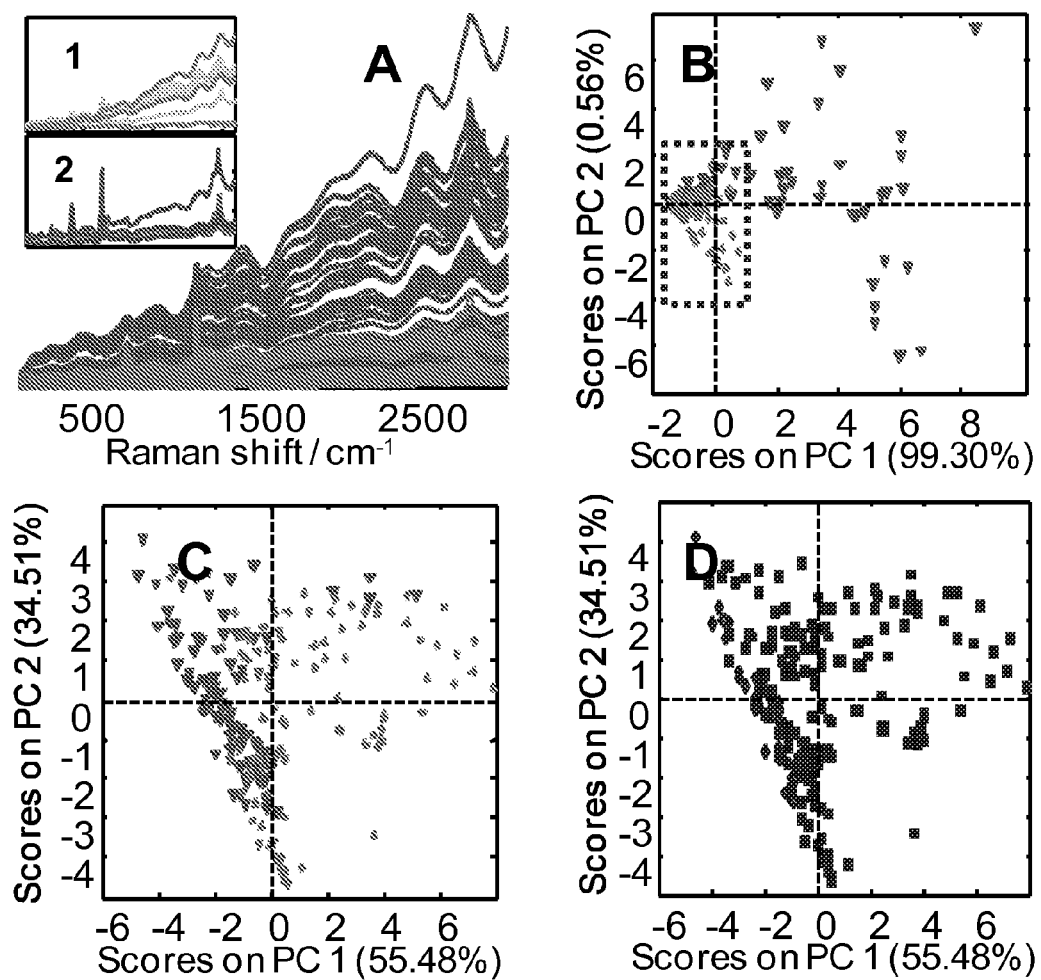
FIGS. 7A-D show the variability of the Raman spectra of GSR particles produced by 0.38 and 0.40 caliber ammunition.

Raman Spectroscopy of Gunshot Residue for Differentiating 0.38 and 0.40 Caliber Ammunition Visual analysis reveals the high variability of Raman spectra reflecting the heterogeneous character of GSR. FIG. 7A, inlay 1 presents Raman spectra recorded from two different particles from the same gunshot sample (0.38 caliber). These spectra have different shapes and fluorescent backgrounds. Similar behavior was found for spectra collected from 0.40 caliber samples (FIG. 7A, inlay 2). Overall, spectral heterogeneity of GSR was observed at each level, including single particles, particles originated from the same discharge, between discharges of the same firearm, and, finally, between firearms. Direct comparison of 0.38 and 0.40 data sets (FIG. 7A) does not give apparent criteria for caliber identification, except for a strong fluorescent background which characterizes 35% of spectra collected from 0.38 caliber particles. As expected, PCA analysis of the raw Raman spectra shows a good separation of this 35% fraction (FIG. 7B, red triangles outside of the dotted rectangle), but the remaining data (100% of 0.40 caliber and 65% of 0.38 caliber data) are overlapped. PCA analysis of normalized, by area, spectra was performed in order to eliminate the effect of total intensity variation. The score plot (FIG. 7C) is scattered, reflecting the spectral shape instability (FIG. 7, inlays 1, 2). Nevertheless, there are regions shown in FIG. 7C which are dominated only by one of two calibers. To reveal that fluorescence does not correlate with the observed differentiation, the score plot was modified using a new coloring scheme (FIG. 7D). Blue squares and purple diamonds represent the spectra falling inside and outside of the dotted rectangle in FIG. 7B, respectively.

Support vector machines (SVM) classification (Wise et al., "PLS Toolbox 3.5 for Use with Matlab.," Vol. 17, Eigenvector Research Inc:Manson, Wash. (2005); (Thissen et al., "Multivariate Calibration with Least-Squares Support Vector Machines," Anal. Chem. 76(11):3099-3105 (2004), which is hereby incorporated by reference in its entirety) was utilized to improve the discrimination between 0.38 and 0.40 caliber GSR particles. The SVM classification model consists of a number of support vectors and non-linear coefficients, which are able to map irregularities in the input variables distribution. The SVMDA algorithm of the PLS Toolbox (Eigenvector Research, Inc) performed with radial basis function (RBF) as a kernel was used. Data compression was performed using PCA with the number of principle components determined by significant factor analysis (Malinowski, E. R., *Factor Analysis in Chemistry*, 3 Ed., New York: John Wiley & Sons, Inc. (2002), which is hereby incorporated by reference in its entirety). The training dataset was composed of 100 Raman spectra, 50 for each 0.38 and 0.40 caliber GSR particles. Leave-one-out cross-validations were performed in order to validate the SVMDA calibration results. All spectra were subsequently eliminated one at a time, and the SVM model based on remaining spectra was used to identify the caliber of the omitted spectrum. Secondly, all spectra collected from the same GSR particle were subsequently eliminated and the remaining spectra were used to assign the caliber of the omitted GSR particle (GSR particle based leave-one-out cross-validation). Discharge sample based leave-one-out cross-validation was performed as the third step. The quality of prediction was then assessed by calculating the correlation between the predicted and actual calibers (see Table 2).

TABLE 2

SVM Classification of the GSR Particles.

| Leave-one-out cross-validation | Quality of prediction, % | |
|---|---|---|
| | Full data set including Raman spectra with strong fluorescent contribution | Data set without Raman spectra with strong fluorescent contribution |
| 1 | 2 | 3 |
| Single spectrum based | 98.5 | 99 |
| GSR particle based | 91 | 97 |
| Discharge sample based: | | |
| Shot 1 cal 0.38 | 75 | 75 |
| Shot 2 cal 0.38 | 100 | 100 |
| Shot 3 cal 0.38 | 100 | 100 |
| Shot 4 cal 0.38 | 95 | 100 |
| Shot 5 cal 0.38 | 100 | 100 |
| Shot 1 cal 0.40 | 60 | 90 |
| Shot 2 cal 0.40 | 70 | 85 |
| Shot 3 cal 0.40 | 55 | 95 |
| Shot 4 cal 0.40 | 95 | 100 |
| Shot 5 cal 0.40 | 95 | 100 |
| Overall | 82.5 | 94.5 |

The single spectrum and GSR particle based leave-one-out cross-validations method correctly assign Raman spectra 98.5 and 91% of the time, respectively. The lowest quality of prediction was obtained during the discharge sample based cross-correlation analysis. Only 60 and 55% of spectra were assigned appropriately for the first and third gunshot from the 0.40 caliber samples. While Raman spectra originating from 0.38 caliber GSR particles were identified correctly, 0.40 caliber spectra were often misclassified (see Table 2, second column). SVM analysis of the modified data set gives more reliable results. Here, all spectra which appear outside of the blue dotted rectangle in FIG. 7B were considered as already classified (classification by fluorescence) and only spectra within the dotted rectangle were used to form a reduced data set for the following SVM analysis. The third column of Table 2 contains the results of SVM identification combined with the classification by fluorescence. For example, of the twenty spectra for the fourth 0.38 caliber discharge sample, five spectra were classified by fluorescence and the remaining spectra were classified by SVM analysis. This accounts for the 100% quality of prediction (see Table 2, third column). The average absolute error of caliber prediction does not exceed 6%.

Example 4

Raman Spectroscopy of Gunshot Residue for Differentiating 0.38 and 9 mm Caliber Ammunition The goal of this study was to differentiate GSR particles originating from 0.38 and 9 mm (~0.35) caliber samples. A 785 nm excitation was used instead of 406.7 nm excitation previously used.

Figure 8:
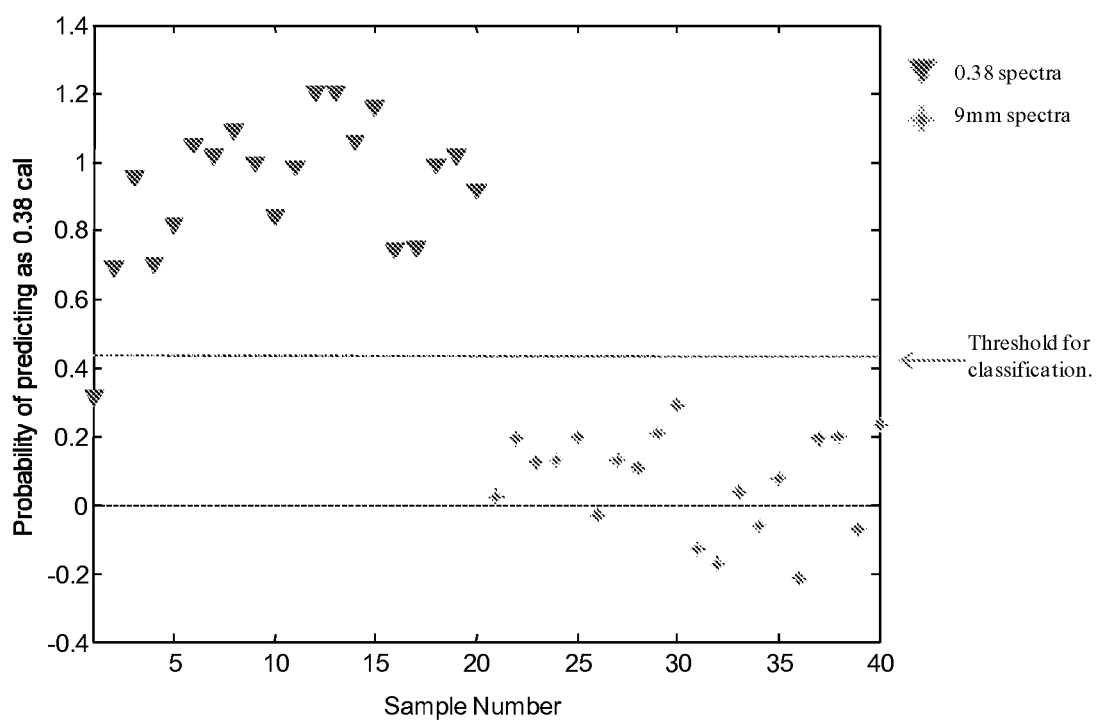
FIG. 8 shows the likelihood of classifying 0.38 and 9 mm spectra as originating from a 0.38 caliber GSR particle. On this plot Raman spectra, which can be easily assigned to the calibers, fall far from the threshold line.

Raman spectra were measured for a total of forty (40) particles (20 for each caliber) and subjected to classification analysis. The resulting plot (FIG. 8) illustrates the probability (Y-axis) of classifying each individual spectrum (X-axis) as being produced by the 0.38 caliber ammunition. The dotted red line can be considered the threshold for classification. Therefore any data points above that line (increasing in probability) are considered to be produced by the 0.38 caliber ammunition. As illustrated in the plot, nineteen out of twenty (red) spectra were correctly classified as being produced by the 0.38 caliber ammunition. Additionally, zero of the twenty 9 mm samples were incorrectly classified as 0.38. Again, this example illustrates the power of Raman spectroscopy combined with advanced statistics for differentiating of ammunition based of gunshot residue.

Raman spectra obtained for both 0.38 and 0.40 cal samples showed significant variation of shape and the fluorescent background. To account for these variations, the source separation (PCA) and multivariate calibration (SVM) methods were combined. Source separation was used to handle variations in the fluorescence contribution. The position and relative intensity of Raman bands were analyzed by SVMDA algorithm. Leave-one-out cross validation reveals the exhaustiveness of the caliber identification. The average absolute error of prediction assessed by calculating the correlation between the predicted and actual calibers did not exceed 6%.

Caliber determination via nondestructive GSR analysis is a novel advancement to crime scene forensics. The method of the present invention has the potential to greatly reduce the time, expense, and basis related to GSR identification. Factors other than caliber size can be examined in order to determine their affect (if any) on the chemical nature of GSR. These factors include but are not limited to chemical composition of the propellant, primer, projectile and cartridge case, age and location of the collected GSR sample, the type of firearm and firing mechanism used in the incident, as well as the condition and age of the discharging firearm. It is also important to determine what species are responsible for the spectroscopic signature of GSR. Common Raman peaks can be linked to components in the primer and propellant.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of identifying ammunition type or weapon type used to fire the ammunition from gunshot residue, said method comprising:
providing a statistical model for identifying ammunition type or weapon type, wherein the statistical model for identifying ammunition type or weapon type is based on principle component analysis (PCA) and support vector machines (SVM), support vector machines discriminant analysis (SVMDA), or partial least squares discriminant analysis (PLS-DA) and based on spectroscopic signatures of the known samples comprising gunshot residues from known types of ammunition or types of weapons used to fire the ammunition;
providing a sample comprising gunshot residue;
subjecting the sample to spectroscopic analysis to produce a spectroscopic signature for the sample, wherein the spectroscopic analysis is selected from the group consisting of Raman spectroscopy and infrared spectroscopy and the spectroscopic signature is obtained from the spectra at: different locations on a single particle of gunshot residue; different particles of gunshot residue from a single discharge; particles of gunshot residue from different discharges of the same firearm; or particles of gunshot residue from different discharges of different firearms; and
applying the spectroscopic signature for the sample to the statistical model to ascertain the type of ammunition or the type of weapon used to fire the ammunition.

2. The method of claim 1, wherein the statistical model is for identifying the type of ammunition.

3. The method of claim 1, wherein the statistical model is for identifying the type of weapon used to fire the ammunition.

4. The method of claim 1, wherein the statistical model is for identifying the type of ammunition which is selected from the group consisting of 9 mm caliber, .45 caliber, .40 caliber, .22 L caliber, and .38 Special.

5. The method of claim 1, wherein the spectroscopic analysis is Raman spectroscopy.

6. A method of establishing a statistical model for determination of ammunition type or weapon type used to fire the ammunition, said method comprising:
providing known samples comprising gunshot residues from known types of ammunition or types of weapons used to fire the ammunition;
subjecting each known sample to spectroscopic analysis to produce a spectroscopic signature for each known sample, wherein the spectroscopic analysis is selected from the group consisting of Raman spectroscopy and infrared spectroscopy and the spectroscopic signature is obtained from the spectra at: different locations on a single particle of gunshot residue; different particles of gunshot residue from a single discharge; particles of gunshot residue from different discharges of the same firearm; or particles of gunshot residue from different discharges of different firearms; and
establishing a statistical model based on principle component analysis (PCA) and support vector machines (SVM), support vector machines discriminant analysis (SVMDA), or partial least squares discriminant analysis (PLS-DA) for determination of the type of ammunition or the type of weapon used to fire ammunition based on the spectroscopic signature obtained for each known sample subjected to spectroscopic analysis.

7. The method of claim 6, wherein the spectroscopic analysis is Raman spectroscopy.

8. The method of claim 1, wherein the spectroscopic analysis is infrared spectroscopy.

9. The method of claim 8, wherein the infrared spectroscopy is Fourier transform infrared spectroscopy.

10. The method of claim 6, wherein the spectroscopic analysis is infrared spectroscopy.

11. The method of claim 10, wherein the infrared spectroscopy is Fourier transform infrared spectroscopy.

12. The method of claim 5, wherein the Raman spectroscopy is selected from the group consisting of conventional Raman spectroscopy, Raman microspectroscopy, surface enhanced Raman spectroscopy (SERS), tip enhanced Raman spectroscopy (TERS), and coherent anti-Stokes Raman spectroscopy (CARS).

13. The method of claim 7, wherein the Raman spectroscopy is selected from the group consisting of conventional Raman spectroscopy, Raman microspectroscopy, surface enhanced Raman spectroscopy (SERS), tip enhanced Raman spectroscopy (TERS), and coherent anti-Stokes Raman spectroscopy (CARS).

14. The method of claim 6, wherein the statistical model is for determination of ammunition type.

15. The method of claim 6, wherein the statistical model is for determination of weapon type.

\* \* \* \* \*